United States Patent
Schmidtke et al.

(10) Patent No.: US 11,857,676 B1
(45) Date of Patent: Jan. 2, 2024

(54) COMPOSITIONS FOR ORAL PAIN RELIEF

(71) Applicant: ORCA Products, LLC, Dothan, AL (US)

(72) Inventors: Craig Schmidtke, Dothan, AL (US); John Graham, Dothan, AL (US)

(73) Assignee: ORCA PRODUCTS, LLC, Dothan, AL (US)

( * ) Notice: Subject to any disclaimer, the term of this patent is extended or adjusted under 35 U.S.C. 154(b) by 12 days.

(21) Appl. No.: 17/407,593

(22) Filed: Aug. 20, 2021

Related U.S. Application Data

(60) Provisional application No. 63/068,128, filed on Aug. 20, 2020.

(51) Int. Cl.
| | |
|---|---|
| *A61K 9/00* | (2006.01) |
| *A61K 31/047* | (2006.01) |
| *A61P 23/02* | (2006.01) |
| *A61K 36/9064* | (2006.01) |
| *A61K 47/26* | (2006.01) |
| *A61K 36/534* | (2006.01) |
| *A61K 31/085* | (2006.01) |
| *A61K 31/045* | (2006.01) |
| *A61K 36/53* | (2006.01) |
| *A61K 47/10* | (2017.01) |

(52) U.S. Cl.
CPC ............ *A61K 9/006* (2013.01); *A61K 31/045* (2013.01); *A61K 31/047* (2013.01); *A61K 31/085* (2013.01); *A61K 36/53* (2013.01); *A61K 36/534* (2013.01); *A61K 36/9064* (2013.01); *A61K 47/10* (2013.01); *A61K 47/26* (2013.01); *A61P 23/02* (2018.01)

(58) Field of Classification Search
None
See application file for complete search history.

(56) References Cited

U.S. PATENT DOCUMENTS

| | | | | |
|---|---|---|---|---|
| 3,860,704 | A * | 1/1975 | Gansen, Jr. | A61K 6/50 106/35 |
| 5,512,278 | A * | 4/1996 | Mundschenk | A61Q 17/005 514/902 |
| 5,989,604 | A * | 11/1999 | Wolf | A61K 8/22 426/805 |
| 7,662,414 | B1 * | 2/2010 | Lawlor | A01K 15/026 426/573 |
| 8,715,625 | B1 * | 5/2014 | Rokitowski | A61K 8/9739 501/63 |
| 8,956,593 | B2 * | 2/2015 | Burgess | A61K 8/19 424/49 |
| 10,583,074 | B2 * | 3/2020 | Xu | A61K 8/36 |

FOREIGN PATENT DOCUMENTS

JP    6336324 B2 *  6/2018

OTHER PUBLICATIONS

RX list information sheet, Aug. 15, 2019) (Year: 2019).*
GelFoam Dental Sponge (RX list information sheet, Aug. 15, 2019) (Year: 2019).*

* cited by examiner

*Primary Examiner* — Melissa S Mercier
(74) *Attorney, Agent, or Firm* — Maynard Nexsen PC; Erin R. Gaddes

(57) ABSTRACT

The present disclosure relates to compositions and methods for treating oral pain. The compositions disclosed herein may comprise a dissolvable carrier containing at least one active ingredient. In some embodiments, the active ingredients comprise guaiacol, eugenol, glycerin, menthol oil, peppermint oil, oregano oil, and cardamom oil. The methods disclosed herein comprise treating oral pain in a subject using the compositions disclosed herein, wherein such compositions are configured as a paste that can be molded on or about a surface exhibiting oral pain in a subject's oral cavity. Such compositions are resistant to the moist environment of the subject's oral cavity and provide rapid, effective pain relief in the subject.

10 Claims, 1 Drawing Sheet

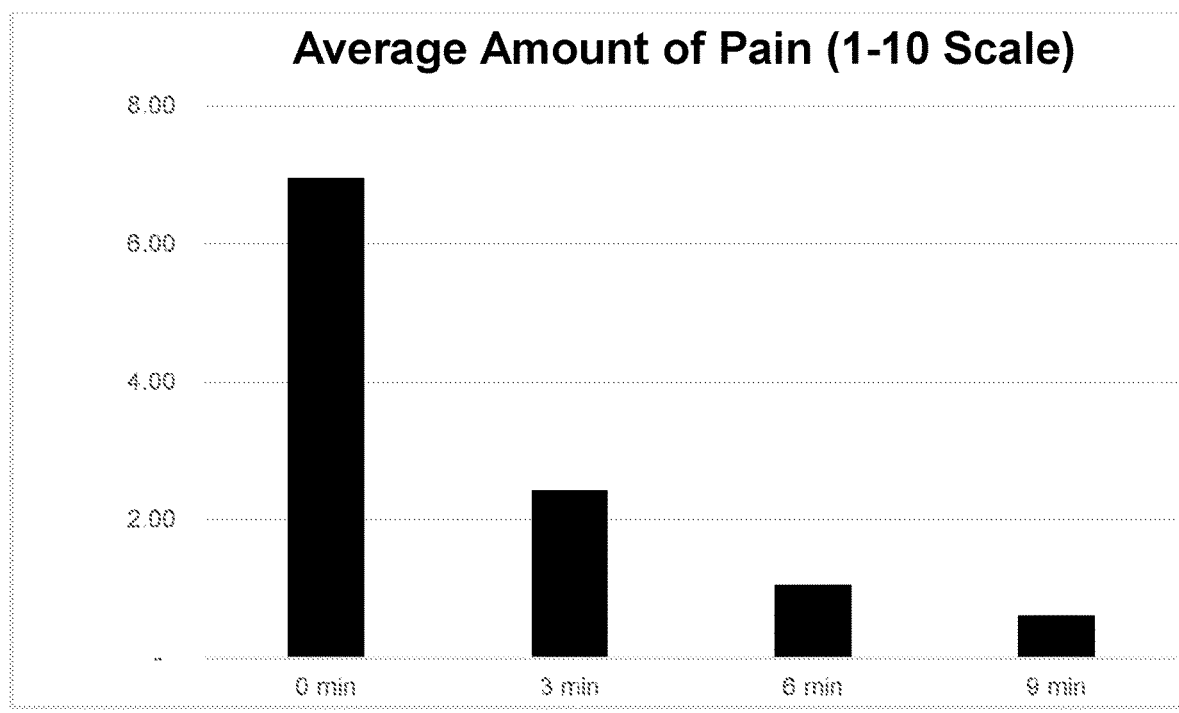

COMPOSITIONS FOR ORAL PAIN RELIEF

RELATED APPLICATION

This application claims priority to U.S. Provisional Application No. 63/068,128, filed on Aug. 20, 2020 and titled "Compositions for Oral Pain Relief," the entire contents of which are incorporated herein by reference.

BACKGROUND OF THE INVENTION

Oral pain is a common, and often serious, problem for many individuals and may arise from a number of conditions. Dry socket, for example, is a common occurrence in the U.S., often occurring in connection with tooth extraction, particularly extraction of the third molar. A dry socket occurs where a blood clot prematurely dislodges from the extraction site and causes the patient to experience significant pain. The socket has sensitive, bony walls that can cause discomfort when exposed to cold or hot temperatures, for example from cold air or beverages. Other painful or irritating conditions of the mouth include, but are not limited to, herpes labialis (cold sores), aphthous stomatitis (canker sores), oral mucositis (stomatitis), thermal burns and pressure sores (decubitus ulcers). Oral pain may also arise from denture use, orthodontics, teeth and gum cleaning, oral cancer, and teething.

In the case of dental procedures, anesthetic compounds such as benzocaine and lidocaine are formulated for application to the area of the procedure through either topical application or injection. These formulations prevent and suppress pain by reversibly blocking the action potentials—primarily sodium channels—responsible for nerve conduction. While effective, the U.S. Food and Drug Administration (FDA) has warned that "[a]dverse events consistent with high systemic exposure to these products include seizures and cardiac arrhythmias."

Currently, the typical treatment for self-care of oral pain includes a number of over-the-counter medications, which often provide only temporary and/or insufficient pain relief. Some of these medications have inadequate efficacy in treating oral lesions due to insufficient contact time with the lesion—often only a matter of seconds. Given the limited efficacy of conventional treatments for painful conditions of the mouth, a need remains for oral pain relief formulations that may remain in contact with the afflicted site for a longer period of time, offering superior pain relief.

SUMMARY OF THE INVENTION

In some embodiments, the present disclosure relates to a composition for oral pain relief comprising: a carrier; and at least one active ingredient that is selected from the group consisting of: guaiacol, eugenol, glycerin, menthol oil, peppermint oil, oregano oil, and cardamom oil. In some embodiments of the composition, the at least one active ingredient comprises about 5% to 30% by weight of the composition. In some embodiments of the composition, the at least one active ingredient comprises about 10% by weight of the composition. In some embodiments of the composition, the at least one active ingredient comprises guaiacol, eugenol, glycerin, menthol oil, peppermint oil, oregano oil, and cardamom oil. In some embodiments of the composition, guaiacol, eugenol, and glycerin collectively comprise about 70% by weight of the at least one active ingredient, menthol oil and peppermint oil each comprise about 10% by weight of the at least one active ingredient, and oregano oil and cardamom oil each comprise about 5% by weight of the at least one active ingredient. In some embodiments of the composition, the carrier comprises xylitol and aloe. In some embodiments of the composition, the carrier is a gelfoam. In some embodiments of the composition, the carrier is a surgical sponge. In some embodiments of the composition, the carrier is dissolvable. In some embodiments of the composition, the composition further comprises at least one flavoring agent. In some embodiments of the composition, the composition further comprises at least one preservative.

In some embodiments, the present disclosure relates to a dissolvable composition for oral pain relief comprising: a carrier, wherein the carrier comprises xylitol and aloe; active ingredients, wherein the active ingredients comprise guaiacol, eugenol, glycerin, menthol oil, peppermint oil, oregano oil, and cardamom oil; and at least one flavoring agent. In some embodiments of the composition, the active ingredients comprise about 5% to 30% by weight of the composition. In some embodiments of the composition, the active ingredients comprise about 10% by weight of the composition. In some embodiments of the composition, guaiacol, eugenol, and glycerin collectively comprise about 70% by weight of the active ingredients, menthol oil and peppermint oil each comprise about 10% by weight of the active ingredients, and oregano oil and cardamom oil each comprise about 5% by weight of the active ingredients. In some embodiments of the composition, the composition further comprises at least one preservative.

In some embodiments, the present disclosure relates to a method of treating oral pain in a subject, comprising the step of applying a composition topically in the subject's oral cavity, wherein the composition comprises a carrier and at least one active ingredient that is selected from the group consisting of: Guaiacol, eugenol, glycerin, menthol oil, peppermint oil, oregano oil, and cardamom oil. In some embodiments of the method, the composition is applied within, on or about a dry socket. In some embodiments of the method, the at least one active ingredient comprises guaiacol, eugenol, glycerin, menthol oil, peppermint oil, oregano oil, and cardamom oil. In some embodiments of the method, guaiacol, eugenol, and glycerin collectively comprise about 70% by weight of the at least one active ingredient, menthol oil and peppermint oil each comprise about 10% by weight of the at least one active ingredient, and oregano oil and cardamom oil each comprise about 5% by weight of the at least one active ingredient. In some embodiments of the method, the carrier comprises xylitol and aloe. In some embodiments of the composition, the carrier comprises a gelfoam. In some embodiments of the composition, the carrier comprises a surgical sponge. In some embodiments of the method, the carrier comprises at least one flavoring agent. In some embodiments of the method, the carrier comprises at least one preservative.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 1 is a histogram displaying the average self-reported oral pain on a scale of 1 to 10 immediately prior to, and 3, 6, and 9 minutes after, administration of the composition disclosed herein.

DETAILED DESCRIPTION

The present disclosure relates to compositions and methods for treating oral pain. The compositions disclosed herein may comprise a dissolvable carrier containing at least one active ingredient. In some embodiments, the active ingredients comprise guaiacol, eugenol, glycerin, menthol oil, peppermint oil, oregano oil, and cardamom oil. The methods disclosed herein comprise treating oral pain in a subject using the compositions disclosed herein, wherein such compositions are configured as a paste that can be molded on or about a surface exhibiting oral pain in a subject's oral cavity. Such compositions are resistant to the moist environment of the subject's oral cavity and provide rapid, effective pain relief in the subject.

The term "active ingredient" as used herein means an ingredient that may be administered to a subject to treat or prevent a disease, condition or symptom that would adversely affect the subject. Active ingredients may include, but are not limited to, anti-inflammatory agents, anti-microbial agents, and other agents known to those of skill in the art. Non-limiting examples of active ingredients include guaiacol, eugenol, glycerin, menthol oil, peppermint oil, oregano oil, and cardamom oil.

The term "carrier" as used herein means a physiologically acceptable carrier of one or more active ingredients for oral application to a subject. As a preferred embodiment, the carrier is a dissolvable paste comprising xylitol and aloe. In some embodiments, the carrier is configured to adhere to a surface in a subject's oral cavity and dissolve overtime. Alternatively, the carrier is a gelfoam formulation, for example Surgifoam® available from Ethicon. The carrier can also be a surgical sponge, for example the absorbable gelatin sponge Gelita-Spon® available from Gelita Medical.

The term "dissolvable" as used herein means substances that, upon administration to a subject, dissolve over time upon exposure to saliva and other mouth fluids.

The term "effective amount" means an amount of an active ingredient that is sufficient to at least reduce or relieve the condition, symptom or disease being treated in a subject, but sufficiently low to avoid any adverse side effects in the subject. The effective amount of the active ingredient may vary with the type and/or severity of the disease, symptom or condition, the age and physical condition of the subject being treated, the duration of treatment, the nature of concurrent therapy, the specific form (i.e., salt) of the pharmaceutically active agent employed, and the particular carrier in which the active ingredient is applied.

The term "oral pain" as used herein means discomfort or pain in a subject within or about a subject's oral cavity. Examples of oral pain include, but are not limited to, pain and/or discomfort in a subject resulting from dry socket, herpes labialis (cold sores), aphthous stomatitis (canker sores), oral mucositis (stomatitis), thermal burns, pressure sores (decubitus ulcers), tooth sensitivity (dentin hypersensitivity), oral cancer, and discomfort or pain caused from dentures, teething, orthodontics, and inflammation.

The term "subject" as used herein means a human or other mammal.

As used herein, "treatment" means that administration of the composition that prevents, alleviates, ameliorates, inhibits, or mitigates one or more symptoms of a condition in a subject.

Disclosed herein are compositions for oral pain relief. In an exemplary composition, the composition comprises a dissolvable carrier comprising xylitol and aloe and active ingredients comprising guaiacol, eugenol, glycerin, menthol oil, peppermint oil, oregano oil, and cardamom oil. In some embodiments, the guaiacol, eugenol, and glycerin collectively comprise about 70% by weight of the active ingredients, menthol oil and peppermint oil each comprise about 10% by weight of the active ingredients, and oregano oil and cardamom oil each comprise about 5% by weight of the active ingredients. In some embodiments, the guaiacol, eugenol, and glycerin collectively comprise about 77.5% by weight of the active ingredients, menthol oil and peppermint oil each comprise about 16% by weight of the active ingredients, and oregano oil and cardamom oil each comprise about 6.5% by weight of the active ingredients. Other carriers and active ingredients, or other percentages by weight of the components thereof, that possess sufficient viscosity and/or adherence may be used as known to those of skill in the art. For example, the carrier may be a surgical sponge, such as the absorbable gelatin sponge Gelita-Spon® available from Gelita Medical, and the one or more active ingredients can be soaked into or absorbed by the carrier.

The compositions disclosed herein may include an effective amount of one or more active ingredients, the amount of which will vary depending on the particular active ingredient. The amount of active ingredient(s) in the carrier according to the present disclosure is about from about 0.01% to about 80% by weight, preferably from about 2.5% to about 40% by weight, and more preferably from about 5% to about 30% by weight.

The composition may further comprise one or more flavoring agents. Suitable flavoring agents include both natural and artificial sweeteners such as: Water-soluble sweeteners including but not limited to monosaccharides, disaccharides, and polysaccharides; water-soluble artificial sweeteners including but not limited to soluble saccharin salts; dipeptide-based sweeteners such as L-aspartic acid derived sweeteners including but not limited to aspartame, and neotame; derivatives of naturally-occurring water-soluble sweeteners including but not limited to chlorinated derivatives of sucrose, and sucralose; protein-based sweeteners including but not limited to *Thaumatoccous danielli* (Thaumatin I and II), and combinations thereof. In general, an effective amount of flavoring agent is utilized to provide the level of sweetness or taste desired for a particular composition, and this amount will vary with the particular flavoring agent selected. The effective amount will normally be from about 0.01% to about 10% by weight of the composition. Water-soluble sweeteners are typically used in amounts of from about 0.01% to about 10% by weight, and preferably in amounts of from about 2.0% to about 5.0% by weight of the composition. The other sweeteners described above, other than water-soluble sweeteners are generally used in amounts of from about 0.01% to about 10% by weight, preferably from about 2% to about 8% by weight, and more preferably from about 3% to about 6% by weight of the composition.

The compositions disclosed herein may further comprise one or more preservatives. The one or more preservatives are added in amounts from about 0.001% to about 5%, preferably from about 0.01% to about 1% by weight of the composition. Preferred preservatives include sodium benzoate, potassium sorbate, EDTA, other preservatives known to those of skill in the art, and combinations thereof.

Embodiments of the compositions disclosed herein can be manufactured by mixing one or more active ingredients with equal parts filtered water and heating the resulting mixture to a rolling boil at an approximate temperature of 205° F. While maintaining an approximate temperature of 205° F., the one or more active ingredients and the filtered water are stirred for approximately 24 hours to evaporate the water and to increase the viscosity of the mixture. The temperature is then reduced and the one or more active ingredients are then mixed with glycerin and one or more thickening agents, such as Aloe Vera and xylitol, to achieve the desired texture.

The composition may be packaged as a kit, comprising a composition within a delivery device. The delivery device may include an aperture through which the composition may be dispensed by the subject or other individual applying the composition to the subject's oral cavity. Non-limiting examples of delivery devices include tubes and syringes. Other containers for the composition may be used, including a resealable tub and other containers known to those of skill in the art. Alternatively, the composition may be packaged in individual units, for example a composition packaged in multiple units of approximately 7 grams or other amount suitable for a single application to a site of oral pain.

Also disclosed herein are methods for treatment of oral pain in a subject by applying the compositions disclosed herein topically to a site in the subject's oral cavity. The compositions disclosed herein may be used to prevent, reduce, suppress or eliminate oral pain. Prevention of oral pain, for example, occurs when the compositions disclosed herein are used as local anesthetics, typically prior to a dental procedure. Suppression or elimination of oral pain, for example, occurs when the compositions disclosed herein are applied to a surface in a subject's oral cavity, such as a canker sore or ulcer such that the application of the composition reduces or eliminates the oral pain. When applied to a surface, the compositions disclosed herein can be molded on and about the location of the oral pain. The compositions disclosed herein, for example, can be used to treat a dry socket by applying the composition within, on or about the dry socket. Similarly, the compositions disclosed herein may be applied on or about a canker sore or other source of oral pain in a subject.

The amount of the active ingredient in the composition may be adjusted to deliver a predetermined dose of the active ingredient over a predetermined period of time, which may typically vary from 4 to 24 hours. For example, a composition may be administered every 12 hours to deliver an effective amount of the active ingredient(s) over a period of 12 hours to a subject in need of such administration. An exemplary adult dose of each active ingredient of the disclosed composition may contain from about 1 to 100 mg, and preferably from about 5 to 20 mg, of each active ingredient (e.g., guaiacol).

Administration may be on an as-needed or as-desired basis, for example, once-monthly, once-weekly, or daily, including multiple times daily, for example, at least once daily, from one to about six times daily, from about two to about four times daily, or about three times daily. The amount of respiratory composition administered may be dependent on a variety of factors, including the general quality of health of the subject, and the subject's age, gender, weight, or severity of symptoms.

Treatment of oral pain using the compositions and methods disclosed herein is not limited to human subjects. Domestic animals, such as dogs, cats, and horses often suffer from oral pain and may be treated with the compositions disclosed herein.

Compared to conventional compositions for oral pain relief, the compositions disclosed herein have several advantages. The compositions disclosed herein offer significant and fast-acting pain relief and also are sufficiently tacky and malleable to be easily applied and adhered to the desired location within a subject's oral cavity. The compositions disclosed herein are also resistant to the moist environment of a subject's oral cavity, allowing prolonged contact with the site of oral pain. Further, the composition may serve as a protective barrier at the site of oral pain to prevent the site from further irritations and insults that would otherwise result in additional oral pain or prolong the time required for such oral pain to subside.

The following examples, applications, descriptions and content are exemplary and explanatory, and are non-limiting and non-restrictive in any way.

EXAMPLES

Pain Relief Study

The applicants performed a trial regarding the efficacy of an embodiment of the composition disclosed herein, described in greater detail in "Exemplary Composition" below. In the trial, 180 subjects who presented with oral pain were examined. They collectively had an initial average self-assessed oral pain of 6.95 out of a maximum of 10 on a visual analog scale. The subjects were administered the composition and oral pain was reassessed by the subjects at 0, 3, 6 and 9 minutes after administrations. The level of oral pain was reduced to a collective average of 2.43, 1.06, and 0.62 out of 10 within 3, 6, and 9 minutes, respectively, as shown in FIG. 1.

Exemplary Composition

The ingredients in Table 1 were combined to provide a dissolvable composition, wherein the active ingredients comprised guaiacol, eugenol, glycerin, menthol oil, peppermint oil, oregano oil, and cardamom oil.

TABLE 1

| Ingredient | %/Weight of Total |
|---|---|
| Xylitol | 3% |
| Active Ingredients | 77% |
| Aloe (powder) | 20% |
| TOTAL | 100% |

In an alternative composition, the ingredients in Table 2 were combined to provide a dissolvable composition, comprising aloe powder, xylitol, filtered water, guaiacol, eugenol, menthol crystals, peppermint oil, oregano oil, cardamom oil, and vegetable glycerin.

TABLE 2

| Ingredient | %/Weight of Total |
|---|---|
| Aloe Powder | 55% |
| Xylitol | 21.3% |
| Eugenol | 2.55% |
| Filtered Water | 8.7% |
| Menthol Crystals | 1.45% |
| Peppermint Oil | 0.95% |
| Vegetable Glycerin | 7.52% |
| Guaiacol | 1.55% |
| Oregano Oil | 0.53% |
| Cardamom Oil | 0.45% |
| TOTAL | 100% |

The compositions, methodologies, and the various embodiments thereof described herein are exemplary. Various other embodiments of the compositions and methodologies described herein are possible.

Now, therefore, the following is claimed:

1. A dissolvable composition for oral pain relief comprising:
   a carrier; and
   all of the following active ingredients: guaiacol, eugenol, glycerin, menthol, peppermint oil, oregano oil, and cardamom oil.

2. The composition of claim 1, wherein the active ingredients collectively comprise about 5% to about 30% by weight of the composition.

3. The composition of claim 1, wherein guaiacol, eugenol, and glycerin collectively comprise about 70% by weight of the active ingredients, menthol and peppermint oil each comprise about 10% by weight of the active ingredients, and oregano oil and cardamom oil each comprise about 5% by weight of the active ingredients.

4. The composition of claim 1, wherein guaiacol, eugenol, and glycerin collectively comprise about 77.5% by weight of the active ingredients, menthol and peppermint oil each comprise about 16% by weight of the active ingredients, and oregano oil and cardamom oil each comprise about 6.5% by weight of the active ingredients.

5. The composition of claim 1, wherein the carrier comprises xylitol and aloe.

6. The composition of claim 1, wherein the carrier is a gelfoam.

7. The composition of claim 1, wherein the carrier is a surgical sponge.

8. The composition of claim 1, wherein the carrier is dissolvable.

9. The composition of claim 1, wherein the composition further comprises at least one flavoring agent.

10. The composition of claim 1, wherein the composition further comprises at least one preservative.

\* \* \* \* \*